United States Patent [19]

Cross et al.

[11] 4,017,298

[45] * Apr. 12, 1977

[54] 1,2,4-TRIALKYL-3,5-DIPHENYL-PYRAZOLIUM SALTS AS HERBICIDES

[75] Inventors: Barrington Cross, Rocky Hill; Bryant Leonidas Walworth, Pennington, both of N.J.

[73] Assignee: American Cyanamid Company, Stamford, Conn.

[ * ] Notice: The portion of the term of this patent subsequent to Dec. 30, 1992, has been disclaimed.

[22] Filed: May 2, 1975

[21] Appl. No.: 574,068

[52] U.S. Cl. .............................. 71/92; 260/310 R; 260/311
[51] Int. Cl.² .......................................... A01N 9/22
[58] Field of Search ........................................ 71/92

[56] References Cited

UNITED STATES PATENTS

| | | | |
|---|---|---|---|
| 3,857,692 | 12/1974 | Feeny | 71/92 |
| 3,882,142 | 5/1975 | Walworth et al. | 71/92 |
| 3,929,451 | 12/1975 | Cross et al. | 71/92 |

*Primary Examiner*—Lewis Gotts
*Assistant Examiner*—Catherine W. Mills
*Attorney, Agent, or Firm*—Harry H. Kline

[57] ABSTRACT

There is provided a method for the preemergence and postemergence control of undesirable plant species by the application of a herbicidally effective amount of a 1,2,4-trialkyl disubstituted pyrazolium salt to the foliage of said undesirable plant species, and to soil containing seeds thereof.

14 Claims, No Drawings

1,2,4-TRIALKYL-3,5-DIPHENYLPYRAZOLIUM SALTS AS HERBICIDES

The present invention relates to a method for the control of undesirable plant species by applying to the foliage of said undesirable plants or to soil containing seed of undesirable plants, a herbicidally effective amount of a compound having the formula:

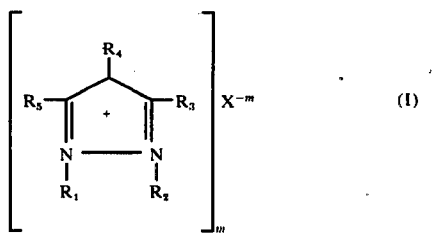

wherein $R_1$ and $R_2$ each represent a $C_2$–$C_4$ alkyl; $R_3$ represents a $C_2$–$C_4$ alkyl, $C_3$–$C_7$ cycloalkyl, phenyl or benzyl; $R_4$ represents a member selected from the group consisting of $C_1$–$C_5$, allyl, propargyl, carbethoxymethyl and benzyl; $R_5$ represents a member selected from the group consisting of $C_3$–$C_7$ cycloalkyl, $C_2$–$C_4$ alkyl and phenyl; X represents an anion having the charge of 1, 2 or 3, and $m$ is 1, 2 and 3.

As is known, certain 1,2-dialkyl-3,5-diphenylpyrazolium salts and a method for the postemergence control of certain undesirable plant species therewith, ae disclosed in Netherlands application for Pat. No. 7,217,015. Additionally, Elguero et al. in *Bull. Soc. Chim. Fr.*, 1121 (1970) describe the compound: 1,2,4-trimethyl-3,5-diphenylpyrazolium iodide. However, no utility for the compound is taught or suggested. Moreover, U.S. Pat. No. 3,818,096, issued on June 18, 1974 to Margaret Sherlock, discloses compositions of 1,2-lower dialkyl arylpyrazolium quaternary salts and a method of lowering blood sugar levels with said compounds. In no way does patentee suggest any preemergence or postemergence herbicidal activity utilizing any pyrazolium salt; nor does patentee suggest the use of any 4-benzyl, 4-propargyl or 4-carbethoxymethyl-1,2-dialkyl-3,5-disubstituted pyrazolium salt having enhanced herbicidal activity.

In the practice of the herbicidal methods of the present invention, compounds which have the hereinabove-defined structure (I) are highly efficacious for the post-emergence control of crabgrass and wild oats and broadleaf weeds, such as lambsquarters, mustard, pigweed, ragweed, velvetleaf and some grass plants. Moreover, they are highly selective in the presence of wheat and rice crops. Unexpectedly, the 4-alkyl compounds are also effective as preemergence herbicides and are useful for the preemergence control of crabgrass and wild oats and broadleaf weeds such as named above.

Among the 4-alkyl derivatives, the 3,5-diphenyl-1,2,4-trimethylpyrazolium salts are especially notable for their outstanding postemergence herbicidal effect on crabgrass and wild oats in the presence of wheat and rice.

The pyrazolium salts of this invention are readily synthesised by reacting an alkali metal salt of an appropriate diketone with an alkylating, alkenylating, alkynylating or benzylating agent. The thus-obtained substituted diketone is further reacted with a $C_1$–$C_4$ alkylhydrazine to yield the appropriately substituted pyrazole. Finally, the thus obtained pyrazole is quaternized with the appropriate $C_1$–$C_4$ alkylating agent to yield the desired pyrazolium salt. The above reaction sequence may be graphically illustrated as follows:

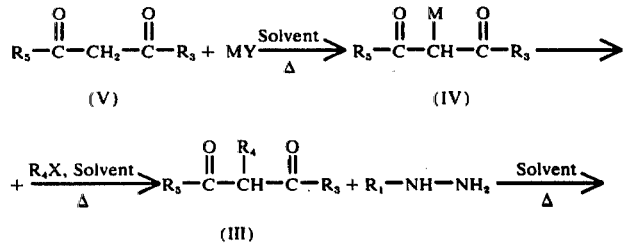

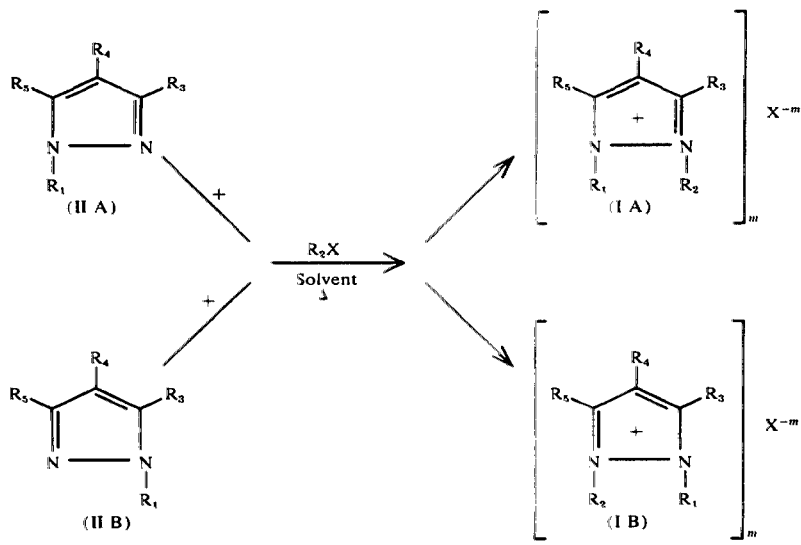

wherein M is an alkali metal, such as sodium, potassium or lithium and Y is hydrogen, hydroxide or alkoxide, such as methoxide, ethoxide, propoxide or butoxide; and wherein $R_1$ to $R_5$, X and m are as above defined. If $R_3 = R_5$, the pyrazolium compound identified as formula (I A) above is obtained.

In general, the alkali metal salt of 1,3-diphenyl-1,3-propanedione or other appropriate diketone can be obtained by reacting an alkali metal hydride, preferably sodium hydride, with said 1,3-diphenyl-1,3-propanedione or other diketone in the presence of a solvent, such as diethylether, methylethyl ether or di-n-propylether. This reaction is usually conducted at a relatively low temperature, i.e., at 0° C. to 20° C. and preferably between 5° C. and 15° reagent. The thus-formed salt is then reacted with an alkylating reagent Illustrative reagents for this reaction include: carbethoxymethyl $C_1$–$C_5$ alkyl halide, allyl halide, propargyl halide, carbethoxymethyl halide and benzyl halides, preferably the iodides, bromides or chlorides of the same.

The reaction is usually carried out at an elevated temperature, generally between about 50° C. and 150° C. and preferably between 50° C. and 100° C., in the presence of an anhydrous solvent such as a dry dialkyl ether, acetone, methyl isobutyl ketone, cyclohexanone, dimethylformamide (DMF) or the like. Generally, about 2 to 3 moles of the alkylating reagent, per mole of the alkali metal ketonic salt are sufficient for effectively completing the reaction.

The thus-formed substituted 1,3-diphenyl-1,3-propanedione or other appropriately substituted diketone is then reacted with a $C_1$–$C_4$ alkylhydrazine.

Since the diketone and the alkylhydrazine compounds combine in equimolar quantities, it is preferable to maintain the molar ratio of reactants at about 1:1; however, a slight excess (up to about 10%) of either reactant may be used.

The ring forming reaction between the diketone and alkyl hydrazine is preferably carried out by combining the reactants in a solvent and heating to the reaction temperature. Suitable temperatures are in the range of from about 70° C to about 150° C and, preferably, between 80° C and 120° C. Suitable solvents include, for example, aprotic solvents, such as, xylene, toluene, benzene, pyridine, DMSO and the like, or protic solvents, such as $C_1$–$C_4$ alcohols, preferably $n$ and i-propanol. Where the latter solvents are employed, high rates of conversion are obtained at temperatures in the range of 80° C to 85° C.

Quaternization of the 1-alkylpyrazole is effected by reaction thereof with at least an equimolar quantity of an $R_2X$ alkylating agent where $R_2$ and X are defined hereinabove. Exemplary agents are methyl chloride, methyl bromide, methyl iodide, dimethyl sulfate, methyl hydrogen sulfate, trimethyl phosphate, methyl-p-toluene sulfonate, and equivalents thereof.

This reaction is preferably conducted in the presence of a solvent, such as, a lower alcohol $C_1$–$C_4$; a ketone, such as, acetone, methyl ethyl ketone, methyl isobutyl ketone or cyclohexanone; an aprotic solvent, such as dimethylsulfoxide or dimethylformamide; or preferably, an aprotic solvent, such as xylene, toluene, benzene or 1,2-dichloroethane.

The quaternization is usually carried out at temperatures maintained between 35° C. and 150° C., preferably between 50° C. and 125° C.

Generally, in the quaternization reaction, the reactants combine in equimolar quantities. It is preferred to employ a 1:1 molar ratio thereof. However, a slight excess (up to 10) of either reactant can be employed. Where the alkylating agent is volatile at the temperatures used, such as in the case of methyl chloride, it is preferred to conduct the reaction in an autoclave. Further, where the diketone selected is asymmetrically substituted and $R_3$ differs from $R_5$ in the pyrazole to be produced, a mixture of isomers will result from the above-described reaction scheme. In such event, it is generally expedient to employ the isomer mixture in the herbicidal processes of the present invention. However, should any separation of the isomers be desired, it can be affected by conventional separation techniques, such as, for example, fractional crystallization.

In carrying out the above ring closure and alkylation reactions, it may be expedient to initially form a salt having an anion other than that which it is desired to employ in the herbicidial processes of the present invention. In such cases, the exchange in anion can be effected by treating the initially formed salt with an ion exchange resin. Among the suitable ion exchange resins, one can mention a strong base organic anion exchanger. Exemplary exchangers contemplate quaternary ammonium salts. Where the resin is supplied as the salt of an anion other than that desired, it is pretreated with an aqueous solution of a salt of the desired anion. For example, if the resin is supplied as a quaternary ammonium chloride and it is desired to produce a pyrazolium nitrate, one would pretreat the resin with an aqueous solution of sodium nitrate.

Other optional subsequent modifications of the anion in the pyrazolium salt may be effected. For example, a pyrazolium chloride may be conveniently converted to the corresponding bromide or iodide by treatment with sodium bromide or sodium iodide, in a solvent, such as acetone. A pyrazolium salt, such as the chloride, may be converted to the corresponding perchlorate by treatment of an aqueous solution of said salt with perchloric acid. This results in the preparation of the less soluble perchlorate salt.

In applying the formula (I) pyrazolium salts to the foliage of the undesirable plant species, the salts are preferably formulated as postemergence herbicidal compositions by admixing a herbicidal adjuvant with a herbicidally effective amount of the salt. Suitable adjuvants include one or more conventional solid or liquid carriers, diluents and formulation aids, particularly surfactants. The salts may be formulated alone, in combination with each other or with other pesticidal agents. The water-miscible (or emulsifiable) concentrates discussed below are especially advantageous. The present invention is further directed thereto as well as to methods for their preparation and use.

Application of the salts as dusts, dust concentrates, wettable powders and water-miscible (or emulsifiable) compositions using conventional application equipment at rates of from 0.27 to 22.4 kg of active ingredient (i.e. cation) per hectare are preferred.

Dusts are generally prepared by grinding together about 1 to 25% by weight of the active agent with from about 99 to 75% by weight of a solid diluent such as kaolin, attapulgite, talc, pumice, diatomaceous earth, fullers earth, wood flour, or the like. Dust concentrates are prepared in similar fashion excepting that about 25 to 95% by weight of the active agent is ground with about 75 to 5% by weight of the diluent.

Wettable powders are prepared in the same manner as the dust concentrates excepting that about 1 to 5% by weight of a surfactant, such as polyoxyethylated vegetable oil, alkyl phenoxy polyoxyethylene ethanol, is also blended with the formulation.

The water-miscible (or emulsifiable) concentrates are prepared by dissolving from 15 to 70% of the compound in 85 to 30% of a water-miscible solvent, such as water itself or another polar water-miscible solvent, such as 2-methoxyethanol, methanol, propylene glycol, diethylene glycol, diethylene glycol monoethyl ether, formamide, and methylformamide. Application of the material is made by adding a predetermined quantity of the water-miscible (or emulsifiable) concentrate to a spray tank and applying as such or in combination with a suitable diluent, such as after addition of a further quantity of water or one of the above polar solvents.

The performance of the product in all of the above formulations, which are applied as liquid sprays, is unexpectedly improved by adding a surfactant or blend of surfactants. Conventional, nonionic surfactants may be employed.

Exemplary nonionic surfactants include alkyl polyoxyethylene ethers, polyoxyethylene (20) sorbitan monolaurate, polyoxyethylene (20) sorbitan monooleate, alkylarypolyglycol ethers, alkyl phenol ethoxylates, trimethyl nonyl polyethylene glycol ethers, alkyl phenol ethylene oxide condensates, octyl phenoxy polyethoxy ethanols, nonylphenyl polyethlyene glycol ethers, condensates of polyoxy ethylenes, polyoxy propylenes, aliphatic polyethers, aliphatic polyesters, alkylaryl polyoxyethylene glycols, and the like.

These surfactants are preferably added to the spray tank at the rate of 0.1% to 5% by volume to provide good wetting of the spray solution on plant foliage.

Herbicidal concentrates containing surfactants are preferably formulated as aqueous sprays containing approximately 29% by weight of the appropriate salt, from about 26 to 50% by weight of water and the remainder of said formulation (26–44% weight) of a selected surfactant. Surfactants, which have been used in preparing suitable surfactants containing concentrates, include an octylphenol ethylene oxide condensate, an ethanolic solution of an alkyl phenol ethoxylate, a polyglycolic ether condensate produced from ethylene oxide and an alkyl phenol and an alkyl aryl polyglycolic ether. Typical formulations are (1) 28.6% of a pyrazolium salt of the present invention, 22.0% of one of the above surfactants and 49.4% water; and (2) 28.6% of a pyrazolium salt of the present invention, 46.7% of one of the above surfactants and 24.7% water.

In control of wild oats, preferably about 4.68 liter, of the concentrate containing surfactant (1) would be admixed with 187 liters of water and applied as a dilute aqueous spray to cover 1 hectare of treated area. This spray solution would contain approximately 0.5% by weight of the surfactant. Formulation (2) would preferably be used in a similar manner except that 4.68 liters of the formulation would be admixed with 374 liters of water and applied as the dilute aqueous spray to cover 1 hectare of treated area.

It is, of course, obvious that the formulations can be varied to provide dilute aqueous sprays containing from about 0.1% to 5.0% by weight of the surfactant and a herbicidally effective amount of the pyrazolium salt.

As previously noted, the water-miscible herbicidal concentrates of the present invention are prepared by dissolving 15% to 70% of a pyrazolium salt of formula (I) in 85% to 30% of a water-miscible polar solvent. These compositions are unexpectedly improved with regard to herbicidal effectiveness by the further step of adding a surfactant. Nonionic surfactants, expecially those having a hydrophilic-lipophilic balance (HLB) of from 11 to 16, are preferred. This conventional surfactant classification test is described, for example, at page 232 et seq of *Emulsion Theory and Practice* by Paul Becher, Rheinholt Publishing Corporation, second edition (1965); also available as No. 162 in the American Chemical Society's Monograph Series.

Preferred methods employ water as the solvent and above one of the pyrazolium salts defined by formula (i) above as the active ingredient.

These compositions are effective for the postemergence control of undesirable plants when applied at a rate sufficient to provide 0.27–22.4 kg/hectare of active ingredient (i.e. cation). Application at rates from about 0.56 kg to 11.2 kg per hectare of said active material are more preferred. For selective postemergence control of wild oats, about 0.56 kg to 3.36 kg per hectare of active material (i.e. cation) are usually preferred.

The present invention and preparation of the starting materials therefor are further illustrated by the following examples which are not to be taken as being limited thereto. Unless otherwise indicated, all parts and percentages are by weight, in the following illustration and examples as well as in the claims and the discussion above.

EXAMPLE 1

Preparation of 2-Sodium-1,3-diphenyl-1,3-propanedione

Dibenzoylmethane (112.3 g, 0.5 mole) is dissolved in anhydrous diethyl ether (2 l). The solution is stirred vigorously and sodium hydride (21.0 g, 0.5 mole) added in portions while maintaining the temperature of the mixture between 7° C. to 12° C. Upon completion of the addition the reaction mixture is allowed to stir 3 hours. Additional anhydrous ether is added, the solid filtered off, reslurried in anhydrous ether, filtered and dried to give 109.0 g (89%) of the sodium salt of 1,3-diphenyl-1,3-propanedione.

EXAMPLE 2

Preparation of 1,3-Diphenyl-2-pentyl-1,3-propanedione n-Pentylbromide (22.6 g, 0.15 mole) is added to an anhydrous solution of 2-sodium-1,3-diphenyl-1,3-propanedione (15.7 g, 0.064 mole) in DMF (150 ml), then the reaction mixture is heated at 80° C to 90° C for 5 days. The reaction mixture is cooled, poured into ice water, stirred for 1 hour, and extracted with chloroform (3×75 ml). Evaporation of the chloroform layer gives an oil which is crystallized from 95% ethanol to give 3.7 g (20%) of product, m.p. 68.5° C to 69.5° C.

Analysis calculated for $C_{20}H_{22}O_2$; C, 81.60; H, 7.53. Found: C, 81.50; H, 7.63.

EXAMPLE 3

Preparation of 2-Benzyl-1,3-diphenyl-1,3-propanedione

Benzylbromide (25.6 g, 0.15 mole) is added to a partial solution of 2-sodium-1,3-diphenyl-1,3-propanedione (15.7 g, 0.064 mole) in dry acetone (200 ml). The reaction mixture is stirred at reflux for 39 hours, cooled and poured into ice water (600 ml). The resulting suspension is filtered, the collected solid is dried and recrystallized from 95% ethanol to give 14.6 g (72%) of product, m.p. 102° C to 103° C.

Analysis calculated for $C_{22}H_{18}O_2$; C, 84.25; H, 5.77. Found: C, 83.35; H, 5.89.

EXAMPLE 4

Employing the procedure of Example 3, above, the following 2-substituted, 1,3-diphenyl-1,3-propanediones are prepared:

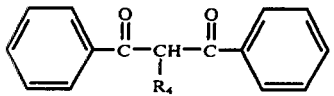

| $R_4$ | Melting Point ° C |
|---|---|
| $CH_3$ | 82–83 |
| $C_2H_5$ | 83–84 |
| $n-C_3H_7$ | 61–62 |
| $i-C_3H_7$ | 81–82 |
| $CH_2-C\equiv CH$ | 98–99 |
| $CH_2-CH=CH_2$ | 64–65 |
| $CH_2-\overset{O}{\overset{\|}{C}}-OC_2H_5$ | 82–83 |
| $n-C_5H_{11}$ | 68.5–69.5 |

EXAMPLE 5

Preparation of 3,5-Diphenyl-4-ethyl-1-methylpyrazole

Methylhydrazine (2.86 g, 0.06 mole) is added to an isopropanol (100 ml) solution of 1,3-diphenyl-2-ethyl-1,3-propanedione (11.0 g, 0.044 mole) with constant stirring at 80° C. The reaction mixture is heated at reflux for 3½ hours, then stirred at room temperature overnight. The reaction mixture is poured into ice-water, stirred for ½ hour, and the resulting mixture extracted with chloroform (3×50 ml). Evaporation of the organic layer gives an oil, which is crystallized from hexane with cooling to give 6.47 g (56%) of product, m.p. 80° C to 81° C.

Analysis calculated for $C_{18}H_{18}N_2$: C, 82.40; H, 6.92; N, 10.68. Found: C, 82.35; H, 7.09; N, 10.75.

EXAMPLE 6

Following the procedure of Example 5 above, the following additional pyrazoles are prepared:

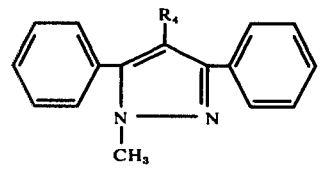

| $R_4$ | Melting Point ° C |
|---|---|
| $CH_3$ | 115–116 |
| $n-C_3H_7$ | 74–75 |
| $i-C_3H_7$ | oil |
| $CH_2-C\equiv CH$ | 159–161 |
| $CH_2-CH=CH_2$ | 79.5–80.5 |
| $n-C_5H_{11}$ | oil |
| $CH_2-\overset{O}{\overset{\|}{C}}-OC_2H_5$ | oil |
| $CH_2-\phenyl$ | 110 |

EXAMPLE 7

Preparation of 3,5-Diphenyl-1,2,4-trimethylpyrazolium methyl sulfate

Dimethylsulfate (7.5 g, 0.06 mole) is added to an anhydrous toluene (100 ml) solution of 1,4-dimethyl-3,5-diphenylpyrazole (10 g, 0.04 mole) at 80° C with stirring. The reaction mixture is stirred at 100° C for 3 hours, cooled and a hygroscopic solid removed by filtration. The solid is dissolved in chloroform and ether is added to the solution gradually. The first fraction which precipitates is extremely hygroscopic, m.p. 94° C to 96° C; the second fraction which precipitates is not hygroscopic, m.p. 103° C to 105° C as the methyl sulfate; total yield of product 12.6 g (72%).

A 5.0 g portion of the product is dissolved in water, the solution filtered and the filtrate treated with saturated sodium iodide solution. The precipitate is filtered off at 10° C, air dried then redissolved in warm water. The aqueous solution is extracted with ether then with chloroform. The chloroform layer is evaporated, the residual oil triturated with ether to afford 2.8 g (54%) of the iodide salt of the above pyrazolium compound as a white solid, m.p. 196° C to 196.5° C.

Similarly, a 3.0 g portion of the pyrazolium methyl sulfate is dissolved in water, the solution filtered and treated with dilute perchloric acid; the precipitate formed is filtered, washed with water and dried to yield 2.5 g (85%) of the perchlorate salt of the above pyrazolium compound. Similarly prepared are:

1,2-Dimethyl-3,5-diphenyl-4-ethylpyrazolium methyl sulfate, m.p. 115° C to 118° C;
1,2-Dimethyl-3,5-diphenyl-4-n-propylpyrazolium perchlorate, m.p. 134° C to 135° C;
1,2-Dimethyl-3,5-diphenyl-4-i-propylpyrazolium perchlorate, m.p. 149° C to 150° C;
1,2-Dimethyl-3,5-diphenyl-4-n-pentylpyrazolium perchlorate, m.p. 51° C to 52.5° C;
1,2-Dimethyl-3,5-diphenyl-4-(2-propynyl)pyrazolium hydrogen sulfate, m.p. 145° C to 151° C;
4-Allyl-1,2-dimethyl-3,5-diphenylpyrazolium hydrogen sulfate, wax;
4-(carboxymethyl)-1,2-dimethyl-3,5-diphenylpyrazolium iodide-, ethyl ester; m.p. 148° C to 149° C;
4-Benzyl-1,2-dimethyl-3,5-diphenylpyrazolium hydrogen sulfate, m.p. 244° C to 246° C;
4-Benzyl-1,2-dimethyl-3,5-diphenylpyrazolium perchlorate, m.p. 180° C to 180.5° C;

EXAMPLE 8

Preparation of 3,5-Dicyclohexyl-1,4-dimethylpyrazole

Methylhydrazine (1.0 g, 0.022 mole) is added at 60° C–70° C with stirring to an isopropanol (200 ml) solution of 1,3-dicyclohexyl-2-methyl-1,3-propanedione (5.0 g, 0.02 mole) having a m.p. =36°–37° C and prepared by the procedure of Example 3 above. The reaction is heated at reflux for 4 hours, then cooled, water (300 ml) added and the resulting solid filtered off. The solid is dissolved in anhydrous toluene, methyl hydrazine (1.0 g, 0.022 mole) added and the reaction mixture heated at 90° C for 4 hours. Then additional methyl hydrazine (1.0 g, 0.022 mole) is added and heating continued for 3 hours. The reaction mixture is cooled. The solvent removed on a rotary evaporator and the resulting solid crystallized from hexane/benzene to give 1.7 g (32%) of the desired product, m.p. 120° C to 122° C.

Analysis calculated for $C_{17}H_{28}N_2$: C, 78.40; H, 10.84; N, 10.76. Found C, 78.38; H, 10.91; N, 10.76.

EXAMPLE 9

Preparation of 3,5-Dicyclohexyl-1,2,4-trimethylpyrazolium methyl sulfate

Dimethyl sulfate (1.26 g. 0.01 mole) is added to an anhydrous toluene (50 ml) solution of 3,5-dicyclohexyl-1,4-dimethylpyrazole (1.7 g, 0.0064 mole) with constant stirring at 80° C. The reaction mixture is then heated to reflux and maintained at reflux, with stirring, for 6 hours. The reaction mixture is cooled, ether (75 ml) is added and the mixture stirred for 3 hours. The resulting solid is filtered and dried to give 1,8 g of the desired product, m.p. 176° C to 177° C.

Analysis calculated for $C_{19}H_{34}N_2O_4S$: C, 59.04; H, 8.87; N, 7.25; S, 8.30. Found: C, 59.62; H, 9.54; N, 7,21; S, 8.04.

EXAMPLE 10

The preemergence activity of the compounds of the present invention is demonstrated by the following tests, wherein a 50/50 acetone/water (v/v) mixture and sufficient test compound to provide the amount per hectare of said compound as indicated in Table I when the mixture is applied to pots planted with seeds or propagules of test plant species.

The pots are prepared the day of herbicide treatment by putting 100 ml of soil in each plastic pot as a base, then morningglory and wild oat seeds are placed on this base and covered with 50 ml (1 cm to 1.37 cm) of soil. Seeds of the other 8 plant species identified below are separately mixed with soil and 50 ml of the soil seed mix added to the pot. The pots are then tamped lightly to level the soil and the soil is wetted with water prior to herbicide application. This prewetting insures that the subsequently applied herbicide treatment solution spreads evenly over the surface of the pot and protects the weed seeds from acetone injury. Each of the 10 weed species is contained in a separate pot. The pots are then arranged in 25.4 × 30.4 cm flats prior to chemical treatment.

The planted pots are treated with 5 ml of test solution and then placed on benches in the greenhouse. Pots are watered after treatment as needed and held in the greenhouse for 3 weeks at which time the results are recorded, as reported in Table (I), below.

| Plant Species Used in Preeemergence Herbicide Evaluation | | |
|---|---|---|
| Common Name | Abbreviation | Scientific Name |
| Lambsquarters | LA | Chenopodium album |
| Wild Mustard | MU | Brassica kaber |
| Pigweed | PI | Amaranthus retroflexus |
| Ragweed | RW | Ambrosia artemisiifolia |
| Morningglory | MG | Ipomoca purpurea |
| Barnyardgrass | BA | Echinochloa crusgalli |
| Crabgrass | CR | Digitaria sanguinalis |
| Green Foxtail | FO | Setaria viridis |
| Wild Oats | WO | Avena fatua |
| Velvetleaf | VL | Abutilon theopharasti |
| Wheat | WH | Triticum vulgare |
| Rice | RI | Oryza sativa |

The rating system used in the evaluation of the experimental data is given below:

| Rating System | % Difference in growth from check* |
|---|---|
| 0 - No effect | 0 |

-continued

| Rating System | % Difference in growth from check* |
|---|---|
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over all effect less than 5 on the rating scale. | |

*Based on visual determination of stand, size, vigor, chlorosis, growth malformation and over-all plant appearance.

and dicotyledonous plants are treated with test compounds dispresed in aqueous acetone mixtures. In the tests, seedling plants are grown in jiffy flats for about 2 weeks. The test compounds are dispersed in 50/50 acetone/water (v/v) mixtures containing 0.5% TWEEN 20, a polyoxyethylene (20) sorbitan monolaurate surfactant by Atlas Chemical Industries, in sufficient quantity to provide the amount per hectare of active compound as indicated in Table II when applied to the plants through a spray nozzle operating at 2.8 kg per $cm^2$ pressure for a predetermined time. After spraying, the plants are placed on greenhouse benches and cared for in the usual manner, commensurate with conventional greenhouse practices. Two weeks after treatment, the seedling plants, with the exception of wild oats which are rated 5 weeks, are examined and rated according to the rating system provided in Example 10.

The plant species used in the postemergence herbicide activity evaluation are the same as those used in the preemergence herbicide evaluation test and are listed in Example 10. The results are reported in Table II.

Table I

Preemergence Herbicidal Activity of 4-Substituted Pyrazolium Salts

| Compound | Treatment kg/ha | LA | MU | PI | RW | MG | BA | CR | FO | WO | VL |
|---|---|---|---|---|---|---|---|---|---|---|---|
| 3,5-Diphenyl-1,2,4-trimethylpyrazolium methyl sulfate | 11.2 | 9 | 9 | 9 | 9 | 0 | 4 | 7 | 2 | 4 | 8 |
| 3,5-Diphenyl-1,2,4-trimethylpyrazolium iodide | 11.2 | 9 | 9 | 9 | | 0 | 3 | 6 | 0 | 7 | 8 |
| 3,5-Diphenyl-1,2,4-trimethylpyrazolium perchlorate | 11.2 | 9 | 9 | 9 | | 0 | 8 | 9 | 0 | 4 | 9 |
| 1,2-Dimethyl-3,5-diphenyl-4-ethyl-pyrazolium methyl sulfate/hydrogen sulfate | 11.2 | 2 | 4 | 9 | 0 | 0 | 0 | 5 | 0 | 0 | 2 |
| 1,2-Dimethyl-3,5-diphenyl-4-n-propyl-propylpyrazolium perchlorate | 11.2 | 2 | 4 | 9 | 4 | 4 | 7 | 8 | 7 | 0 | 6 |
| 1,2-Dimethyl-3,5-diphenyl-4-i-propyl-pyrazolium perchlorate | 11.2 | 3 | 0 | 3 | 0 | 4 | 3 | 7 | 7 | 1 | 0 |
| 1,2-Dimethyl-3,5-diphenyl-4-n-pentylpyrazolium perchlorate | 11.2 | 2 | 0 | 5 | 0 | 0 | 0 | 5 | 5 | 0 | 0 |
| 3,5-Dicyclohexyl-1,2,4-trimethylpyrazolium methyl sulfate | 11.2 | | 4 | 0 | 0 | 0 | 8 | 9 | 5 | 4 | 0 |

EXAMPLE 11

The postemergence herbicidal activity of the compounds of the present invention is demonstrated by the following tests, wherein a variety of monocotyledonous

Table II

Postemergence Herbicidal Activity of 4-Substituted Pyrazolium Salts

| Compound | Treatment kg/ha | LA | MU | PI | RW | MG | BA | CR | FO | WO | VL | WH | RI |
|---|---|---|---|---|---|---|---|---|---|---|---|---|---|
| 3,5-Diphenyl-1,2,4-trimethylpyrazolium methyl sulfate | 11.2 | 9 | 9 | 9 | 9 | 2 | 2 | 0 | 1 | 9 | 8 | | |
| | 4.48 | | 9 | 9 | | 2 | 1 | 5 | 0 | 8 | 8 | 6 | 7 |
| | 1.12 | | 9 | 1 | | 0 | 1 | 3 | 0 | 9 | 7 | 6 | 5 |
| | .56 | | 5 | 0 | | 0 | 1 | 1 | 0 | 9 | 7 | 5 | 5 |
| 3,5-Diphenyl-1,2,4-trimethylpyrazolium iodide | 11.2 | 9 | 9 | 9 | 9 | 2 | 2 | 2 | 3 | 8 | | | |
| | 4.48 | | 9 | 8 | | 8 | 1 | 1 | 0 | 9 | 9 | 7 | 8 |
| | 1.12 | | 9 | 2 | | 0 | 0 | 0 | 0 | 9 | 3 | 6 | 5 |
| | .56 | | 9 | 1 | | 0 | 0 | 0 | 0 | 9 | 3 | 5 | 5 |
| 3,5-Diphenyl-1,2,4-trimethylpyrazolium percholate | 11.2 | 9 | 9 | 9 | 9 | 0 | 2 | 3 | 5 | 9 | 3 | | |
| | 4.48 | | 9 | 6 | | 1 | 5 | 0 | 3 | 9 | 7 | 7 | 0 |
| | 1.12 | | 9 | 7 | | 1 | 2 | 0 | 3 | 9 | 5 | 5 | 0 |
| | .56 | | 5 | 2 | | 1 | 1 | 0 | 2 | 9 | 3 | 2 | 0 |
| 1,2-Dimethyl-3,5-diphenyl-4-ethyl-pyrazolium methyl sulfate/hydrogen sulfate | 11.2 | 9 | 9 | 9 | 9 | 9 | 7 | 1 | 8 | 9 | 9 | | |
| | 4.48 | | 9 | 9 | | 9 | 3 | 5 | 6 | 6 | 9 | 0 | 1 |
| | 1.12 | | 9 | 9 | | 9 | 1 | 5 | 6 | 1 | 6 | 0 | |
| | .56 | | 9 | 9 | | 1 | 0 | 3 | 1 | 0 | 6 | 0 | 0 |
| 1,2-Dimethyl-3,5-diphenyl-4-n-propyl-pyrazolium perchlorate | 11.2 | 9 | 9 | 9 | 7 | 8 | 5 | 5 | 6 | 5 | 7 | | |
| | 4.48 | | 9 | 9 | | 6 | 0 | 5 | 3 | 0 | 3 | 0 | 0 |
| | 1.12 | | 9 | 9 | | 0 | 0 | 5 | 3 | 0 | 2 | 0 | 0 |
| | .56 | | 9 | 9 | | 0 | 0 | 3 | 0 | 0 | 1 | | |
| 4-Benzyl-1,2-dimethyl-3,5-diphenyl-pyrazolium hydrogen sulfate | 11.2 | 9 | 9 | 9 | 0 | 6 | 3 | 0 | 3 | 3 | 8 | | |
| | 4.48 | | 9 | 9 | | 5 | 0 | 1 | 6 | 0 | 5 | 0 | 6 |
| | 1.12 | | 9 | 9 | | | 0 | 0 | 0 | 0 | 1 | 0 | 0 |
| 4-Benzyl-1,2-dimethyl-3,5-diphenyl-pyrazolium perchlorate | 11.2 | 9 | 8 | 9 | 0 | 2 | 1 | 1 | 3 | 3 | 0 | | |
| | 4.48 | | 9 | 8 | | 0 | 0 | 0 | 2 | 0 | 0 | 0 | 0 |
| 1,2-Dimethyl-3,5-diphenyl-4-i-propyl-pyrazolium perchlorate | 11.2 | 9 | 9 | 9 | 3 | 9 | 3 | 2 | 1 | 5 | 8 | | |
| | 4.48 | | 9 | 9 | | 5 | 0 | 5 | 3 | 1 | 3 | 0 | 0 |
| | 1.12 | | 9 | 9 | | 5 | 0 | 5 | 3 | 0 | 1 | 0 | 0 |
| 1,2-Dimethyl-3,5-diphenyl-4-n-pentyl-pyrazolium perchlorate | 11.2 | 9 | 9 | 9 | 3 | 7 | 7 | 0 | 1 | 2 | 9 | | |
| | 4.48 | | 9 | 9 | | 9 | 0 | 0 | 3 | 0 | 7 | 0 | 0 |
| | 1.12 | | 9 | 9 | | 1 | 0 | 0 | 3 | 0 | 2 | 0 | 0 |
| 1,2-Dimethyl-3,5-diphenyl-4-(2-propynyl)- | 11.2 | 9 | 9 | 9 | 5 | 7 | 3 | 2 | 1 | 5 | 9 | | |

Table II-continued

| Compound | Treatment kg/ha | LA | MU | PI | RW | MG | BA | CR | FO | WO | VL | WH | RI |
|---|---|---|---|---|---|---|---|---|---|---|---|---|---|
| Postemergence Herbicidal Activity of 4-Substituted Pyrazolium Salts | | | | | | | | | | | | | |
| pyrazolium hydrogen sulfate | 4.48 | | 9 | 9 | | 9 | 1 | 0 | 2 | 0 | 6 | 0 | 3 |
| | 1.12 | | 6 | 9 | | 9 | 0 | 0 | 0 | 0 | 1 | 0 | |
| 4-Allyl-1,2-dimethyl-3,5-diphenyl-pyrazolium hydrogen sulfate | 11.2 | 9 | 9 | 9 | 3 | 8 | 3 | 3 | 1 | 3 | 9 | | |
| | 4.48 | | 9 | 9 | | 9 | 0 | 0 | 5 | 3 | 6 | 1 | 6 |
| | 1.12 | | 9 | 9 | | 8 | 0 | 0 | 2 | 0 | 5 | 0 | 0 |
| 4-(Carboxymethyl)-1,2-dimethyl-3,5-diphenylpyrazolium iodide-, ethyl ester | 11.2 | 9 | 3 | 8 | 0 | 2 | 0 | 0 | 0 | 1 | 6 | | |
| | 4.48 | | 7 | 9 | | 6 | 0 | 0 | 0 | 0 | 3 | 0 | 0 |
| 3,5-Dicyclohexyl-1,2,4-trimethyl-pyrazolium methyl sulfate | 11.2 | 9 | 9 | 9 | 9 | 7 | 9 | 3 | 8 | 8 | 9 | | |
| | 4.48 | | 9 | 9 | | 9 | 8 | 8 | 7 | 8 | 9 | 1 | 3 |
| | 1.12 | | 8 | 8 | | 9 | 7 | 7 | 5 | 8 | 8 | 0 | |

We claim:

1. A method for the herbicidal control of undesirable plant species comprising: applying to the foliage of said undesirable plant species, or to the soil containing the seeds of said plant species, a herbicidally effective amount of a compound having the formula:

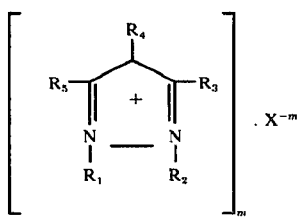

wherein $R_1$ and $R_2$ each represent $C_1$–$C_4$ alkyl, $R_3$ represents a member selected from the group consisting of $C_2$–$C_4$ alkyl, $C_3$–$C_7$ cycloalkyl, phenyl and benzyl; $R_4$ represents a member selected from the group consisting of $C_1$–$C_5$ alkyl, allyl, propargyl, carbethoxymethyl and benzyl; $R_5$ represents a member selected from the group consisting of $C_2$–$C_4$ alkyl, $C_3$–$C_7$ cycloalkyl and phenyl; X represents an anion having the charge of 1, 2 or 3, and $m$ is an integer from 1 to 3.

2. The method according to claim 1, wherein the compound has the structure wherein $R_1$, $R_2$ and $R_4$ are methyl; $R_3$ and $R_5$ are phenyl; X and $m$ are as defined above.

3. The method according to claim 1, wherein said compound is 1,2-dimethyl-3,5-diphenyl-4-ethyl-pyrazolium methyl sulfate/hydrogen sulfate.

4. The method according to claim 1, wherein said compound is 1,2-dimethyl-3,5-diphenyl-4-n-propyl-pyrazolium perchlorate.

5. The method according to claim 1, wherein said compound is 4-benzyl-1,2-dimethyl-3,5-diphenyl-pyrazolium hydrogen sulfate.

6. The method according to claim 1, wherein said compound is 4-benzyl-1,2-dimethyl-3,5-diphenyl-pyrazolium perchlorate.

7. The method according to claim 1, wherein said compound is 1,2-dimethyl-3,5-diphenyl-4-i-propyl-pyrazolium perchlorate.

8. The method according to claim 1, wherein said compound is 1,2-dimethyl-3,5-diphenyl-4-n-pentyl-pyrazolium perchlorate.

9. The method according to claim 1, wherein said compound is 1,2-dimethyl-3,5-diphenyl-4-(2-propynyl)pyrazolium hydrogen sulfate.

10. The method according to claim 1, wherein said compound is 4-allyl-1,2-dimethyl-3,5-diphenyl-pyrazolium hydrogen sulfate.

11. The method according to claim 1, wherein said compound is 4-(carboxymethyl)-1,2-dimethyl-3,5-diphenylpyrazolium iodide-, ethyl ester.

12. The method according to claim 1, wherein said compound is 3,5-dicyclohexyl-1,2,4-trimethyl-pyrazolium methyl sulfate.

13. The method according to claim 1, wherein said compound is applied at the rate of from 0.56 kg. to 11.2 kg. per hectare.

14. The method according to claim 1, wherein said compound is applied at the rate of from 0.56 kg. to 4.48 kg., per hectare.

* * * * *